United States Patent
Bertoncini et al.

(10) Patent No.: US 8,301,397 B2
(45) Date of Patent: Oct. 30, 2012

(54) METHOD OF DETERMINING PHYSICO-CHEMICAL PROPERTIES OF A PETROLEUM SAMPLE FROM TWO-DIMENSIONAL GAS CHROMATOGRAPHY

(75) Inventors: Fabrice Bertoncini, Lyons (FR); Benoît Celse, Genas (FR); Cyril Dartiguelongue, St Symphorien d'Ozon (FR)

(73) Assignee: IFP, Cedex (FR)

( * ) Notice: Subject to any disclaimer, the term of this patent is extended or adjusted under 35 U.S.C. 154(b) by 601 days.

(21) Appl. No.: 12/464,125

(22) Filed: May 12, 2009

(65) Prior Publication Data
US 2009/0282897 A1 Nov. 19, 2009

(30) Foreign Application Priority Data
May 14, 2008 (FR) .................................. 08 02637

(51) Int. Cl.
*G01N 31/00* (2006.01)
(52) U.S. Cl. ............... 702/25; 702/24; 702/28; 702/30; 73/23.36
(58) Field of Classification Search ............... 702/1, 22, 702/25
See application file for complete search history.

(56) References Cited

U.S. PATENT DOCUMENTS

| | | | | |
|---|---|---|---|---|
| 4,645,585 | A * | 2/1987 | White ............................ | 208/58 |
| 5,398,539 | A * | 3/1995 | Gordon et al. ............... | 73/23.35 |
| 6,275,775 | B1 | 8/2001 | Baco et al. | |
| 2008/0180447 | A1 * | 7/2008 | Bertoncini et al. ........ | 345/440.1 |

FOREIGN PATENT DOCUMENTS

| | | |
|---|---|---|
| FR | 2 774 768 | 8/1999 |
| WO | WO 2006/055499 A1 | 5/2006 |

OTHER PUBLICATIONS

Beens, J., Boeles, H., Robert, T. and Blomber, J., Quantitative Aspects of Comprehensive Two-Dimensional Gas Chromatography (GC×GC), Jan. 1998, unknown publisher, vol. 21, pp. 47-54, BNSDOCID: XP-002440106.*

Vendeuvre, C., et al: "Characterisation of Middle-Distillates by Comprehensive Two-Dimensional Gas Chromatography (GC×GC): A Powerful Alternative for Performing Various Standard Analysis of Middle-Distillates", Journal of Chromatography, Elsevier Science Publishers B.V., Amsterdam, NL., vol. 1086, No. 1-2, Sep. 9, 2005, pp. 21-28, XP004995136, ISSN: 0021-9673.

Beens, Jan, et al: "Quantitative Aspects of Comprehensive Two-Dimensional Gas Chromatography (GC×GC)", Journal of Separation Science, Wiley, DE, vol. 21, Jan. 1, 1998, pp. 47-54, XP002440106, ISSN: 1615-9306.

Beens, Jan, et al: "The role of Gas Chromatography in Compositional Analyses in the Petroleum Industry", Trends in Analytical Chemistry, vol. 19, No. 4, Apr. 2000, pp. 260-275, XP002517805, pp. 260-275, XP002517805 Elsevier.

* cited by examiner

*Primary Examiner* — Jonathan C Teixeira Moffat
*Assistant Examiner* — Mischita Henson
(74) *Attorney, Agent, or Firm* — Antonelli, Terry, Stout & Kraus, LLP.

(57) ABSTRACT

A method of determining physico-chemical properties of a petroleum sample from two-dimensional gas chromatography. The amounts of molecular compounds present in the sample are determined by means of two-dimensional gas chromatography. At least one physical property, such as the octane number, is then determined from these amounts. A previously calibrated relation connecting the physical property to the amounts is used to this end.

13 Claims, 4 Drawing Sheets

METHOD OF DETERMINING PHYSICO-CHEMICAL PROPERTIES OF A PETROLEUM SAMPLE FROM TWO-DIMENSIONAL GAS CHROMATOGRAPHY

BACKGROUND OF THE INVENTION

1. Field of the Invention

The present invention relates to the field of physical and chemical analysis of petroleum samples. What is referred to as a "petroleum sample" is a hydrocarbon mixture, that is a mixture of organic compounds mainly containing carbon (C) and hydrogen (H) atoms.

In particular, the invention provides a method of determining physico-chemical properties of a petroleum sample from a quantitative analysis of the molecular composition thereof.

2. Description of the Prior Art

The manufacture of commercial fuels, the optimization and the manufacturing control of the various bases of gasoline pools (gasoline, diesel fuel or kerosene) require precise control of macroscopic physical properties in order to meet market specifications. Macroscopic properties or overall properties are the properties of a petroleum sample that are observed at the scale of the sample, as opposed to the properties that are observed at a smaller scale (molecular compound scale). The macroscopic physical properties are, for example, the octane number, the cetane number, the gravity, etc. Refiners do not have systematically access to the measurement of these physical properties, notably when the amount of fuel available is not sufficient for measurement. Monitoring and optimization of industrial plants producing gasoline pool bases also increasingly requires precise knowledge of the mechanisms involved in the reactors.

Besides, refiners want to predict the impact of a transformation of fuels on the physical properties thereof. For example, it is desired to be able to simulate the effect of a change in the distillation range of a sample, or the effect of the chemical transformation of a family of compounds (hydrogenation of aromatic compounds to saturated cyclic compounds) on properties such as the octane number, the cetane number or the gravity.

In this perspective, knowledge of the macroscopic physical properties of fuels and knowledge of the properties by cuts becomes essential. A cut of a petroleum sample is the distillate obtained between two predetermined temperatures during a distillation operation. Refiners' needs are increasingly directed towards the development of explicit property models as regards the chemical composition of fuels.

Physical methods have been standardized to assess these properties, but they are generally costly in time and they require a large volume of samples for implementing them.

For samples distillable between 0° C. and 220° C. (gasoline and naphtha cuts), these physical methods have been advantageously replaced by the use of cut mixing laws based on the refiners' experience, or by the use of dedicated analytical tools allowing the composition of the products to be related to a physical property. Modern chemical analysis methods such as infrared spectrophotometry (ISP) or gas chromatography (GC) have thus allowed access to more complete molecular information on gasoline cuts, and the development of correlations between the chemical composition of the gasoline obtained by these analysis techniques and several properties such as the octane number, the gravity, the calorific value, etc. The first research work was carried out from gas chromatography (GC) analysis and it is described in the following document: Jenkins G. J., Mc Taggart N. G., Watkin B. L. H., (1968) "GLC for On-Stream Octane Number Rating of Stabilized Catalytic Reformates", Gas Chromatography, Ed. Inst. Petr., London, p 185-198.

Models obtained by linear regression were elaborated. They group together the chromatographic data (mass concentration of the individual constituents (compounds)) into about thirty groups of constituents according to chemical structure analogy. In the early 80s, the first publications relative to the calculation of octane numbers from near infrared spectrometry appeared: Kelly J. J., Barlow C. H., Jinguji T. M. and Callis J. B. (1989) "Prediction of Octane Numbers from Near-Infrared Spectral Features in the Range 660-1212 nm", Analytical Chemistry, Vol 61, No 4, 313. The work by D. Lambert et al. marked the beginning of the use of this technique as a control tool for the gasoline pool of refineries: Espinosa A., Lambert D. and Valleur M. (1995) "Use NIR technology to optimize plant operation, Hydrocarbon Processing", February, 86. According to the same approach, J. P. Durand, Y. Boscher, N. Petroff and M. Berthelin, J. Chromatogr., 395 (1987) 229, showed that it is possible to describe the density, the gravity, the Reid vapour pressure, etc., from a gasoline compositional analysis.

For samples distillable between 220° C. and 450° C. (case of diesel fuel cuts and middle distillates), other techniques had to be developed. In fact, such a compositional detail is not available for diesel fuel cuts or middle distillates that involve severe limitations regarding the aforementioned analysis methods. It is known that the increase in the number of isomers with the number of carbon atoms makes the extension of this degree of information to heavier cuts than gasoline illusory. For GC, the lack of separation power does not allow having a distribution of the hydrocarbons by families. This makes the property prediction models based on a molecular description ineffective. Only the mass distribution of the components as a function of the boiling point is accessible. As for mass spectrometry, only more summary molecular information is available (obtained according to the method referred to as Fitgerald's method (reference number ASTMD2425)). However, this method is applicable only to samples having a well-established range of distillation intervals (set initial and end points, fraction distillable by at least 70° C. in the interval), or limited olefin contents (2% m/m maximum). Besides, it does not allow separate quantification of the linear and branched paraffins, which does not enable determination of some properties that greatly depend on the branching rate (cetane number, gravity, etc.).

Specialists then combine the data obtained by GC, SM or any other informative detector (such as the atomic emission detector AED) to bypass the limitations intrinsic to each one of these techniques and predict the macroscopic properties of the middle distillate or kerosene cuts.

U.S. Pat. No. 5,699,269 describes a method allowing prediction of the macroscopic properties of petroleum cuts from a gas chromatography analysis coupled with mass spectrometry (GC/MS). This method presupposes that the property model calibration basis contains samples whose composition is close to that of the sample to be analyzed. This invention allows prediction of the macroscopic properties of petroleum cuts but it is not applicable to the prediction of cut simulation or chemical transformation simulation properties. In other words, this method is not extrapolatable outside its calibration basis. It does not meet the need for fuel property simulation because it is not based on the properties-fine chemical composition of the fuels link.

U.S. Pat. No. 6,275,775 describes a method of predicting the properties of petroleum fractions by means of gas chromatography coupled to an atomic emission detector (GC-AED). The properties predicted are macroscopic but they also depend on the distillation range of the sample. This invention thus allows deducing from the GC-AED analysis the property profiles of diesel fuels as a function of the distillation curve. On the other hand, it does not allow simulation of a chemical transformation of a petroleum cut (for example the conversion of aromatic compounds to saturated cyclic compounds by a hydrotreatment method).

The approach using near infrared spectrophotometry was also implemented on middle distillates. However, this method is correlative and it greatly depends on the representativity of the database. Furthermore, it is not applicable to the prediction of cut simulation or chemical transformation simulation properties. In other words, this method is not extrapolatable outside its calibration basis. It does not meet the need for fuel property simulation because it is not based on the properties-fine chemical composition of the fuels link.

In conclusion, the known methods are based on correlative models and not on explicative models insofar as they are not based on the molecular detail of the petroleum fractions being analyzed. In particular, the conventional analytical methods for analyzing samples distillable between 150° C. and 450° C., such as diesel fuel cuts, do not provide sufficient analytical detail to allow modelling of the application properties of these samples. The key point for the prediction of properties lies in the close relationship between the property to be predicted and the detailed chemical composition (analysis by families and by number of carbon atoms for example for petroleum products).

SUMMARY OF THE INVENTION

The invention is an alternative method of determining the macroscopic physico-chemical properties of a petroleum sample, allowing overcoming of the limitations of conventional methods. The method achieves this by assessing these properties from quantitative data obtained by two-dimensional gas chromatography. This analysis allows prediction of the macroscopic properties of a sample, to assess these properties for any petroleum cut and to assess the evolution of these properties after chemical transformations of the petroleum sample.

The invention thus relates to a method of determining at least one physical property of a mixture of molecular compounds such as a petroleum sample, comprising:

determining the amounts of n compounds present in the mixture, by use of two-dimensional gas chromatography; and determining the physical property from the amounts, by means of a previously calibrated relation f connecting the physical property to said amounts.

According to the invention, relation f can be defined by: $P_m = f(\alpha_i, Q_i, n)$, where $P_m$ is the physical property, n is the number of molecular compounds separated by chromatography, $\alpha_i$ is a coefficient to be calibrated and associated with a compound i, and $Q_i$ is the amount of compound i determined by chromatography.

This relation f can then be calibrated by carrying out the following steps:

determining amounts of compounds present in at least a second mixture containing at least the n molecular compounds, by means of two-dimensional gas chromatography;

measuring the physical property $P_m$ of the second mixture;

initializing coefficients $\alpha_i$ by assigning the coefficients a known physical property value for a sample containing only compound i;

calculating the physical property by use of the function f;

modifying coefficients $\alpha_i$ to minimize a difference between a value of the calculated physical property and the value of the measured physical property.

Relation f can for example be defined by:

$$f(\alpha_i, Q_i, n) = \sum_{i=n}^{i=n} \alpha_i \cdot Q_i.$$

Two-dimensional gas chromatography can be carried out by means of the following steps:

recording a chromatographic signal comprising chromatographic peaks;

generating a two-dimensional chromatogram with each column corresponding to a portion of the chromatographic signal, the chromatographic peaks forming spots on the chromatogram;

defining the spots with polygons;

adjusting said polygons by:
identifying portions of the chromatographic signal contained between two intersections of the polygon with columns of the chromatogram;
determining start times, end times and maxima for the chromatographic peaks present in the portions;
displacing the intersections according to the start times, the end times and the chromatographic peak maxima;
determining an amount of at least one molecular compound by calculating surface area of the adjusted polygon.

According to the invention, the amount of a compound can be determined by assessing its concentration from the surface area of the polygon.

The physical property can be selected from among the following properties:

combustion properties: octane number, cetane number, smoke point and gravity; and cold properties: cold filter-plugging point, cloud point, pour point and freezing point.

According to the invention, the mixture can advantageously be a petroleum sample distillable between 150° C. and 450° C.

Finally, the invention also relates to a method of predicting a physical property of a cut of a petroleum sample, wherein an effect of a change in the distillation range of the sample on the physical property is simulated by keeping only the part of the chromatographic signal corresponding to this distillation interval and by calculating the physical property according to the method of the invention.

BRIEF DESCRIPTION OF THE FIGURES

Other features and advantages of the method according to the invention will be clear from reading the description hereafter of embodiments given by way of non limitative example, with reference to the accompanying figures wherein:

FIG. 4 illustrates a chromatogram of a diesel fuel, total effluent of a refining plant; wherein

DETAILED DESCRIPTION OF THE INVENTION

Figure 1:
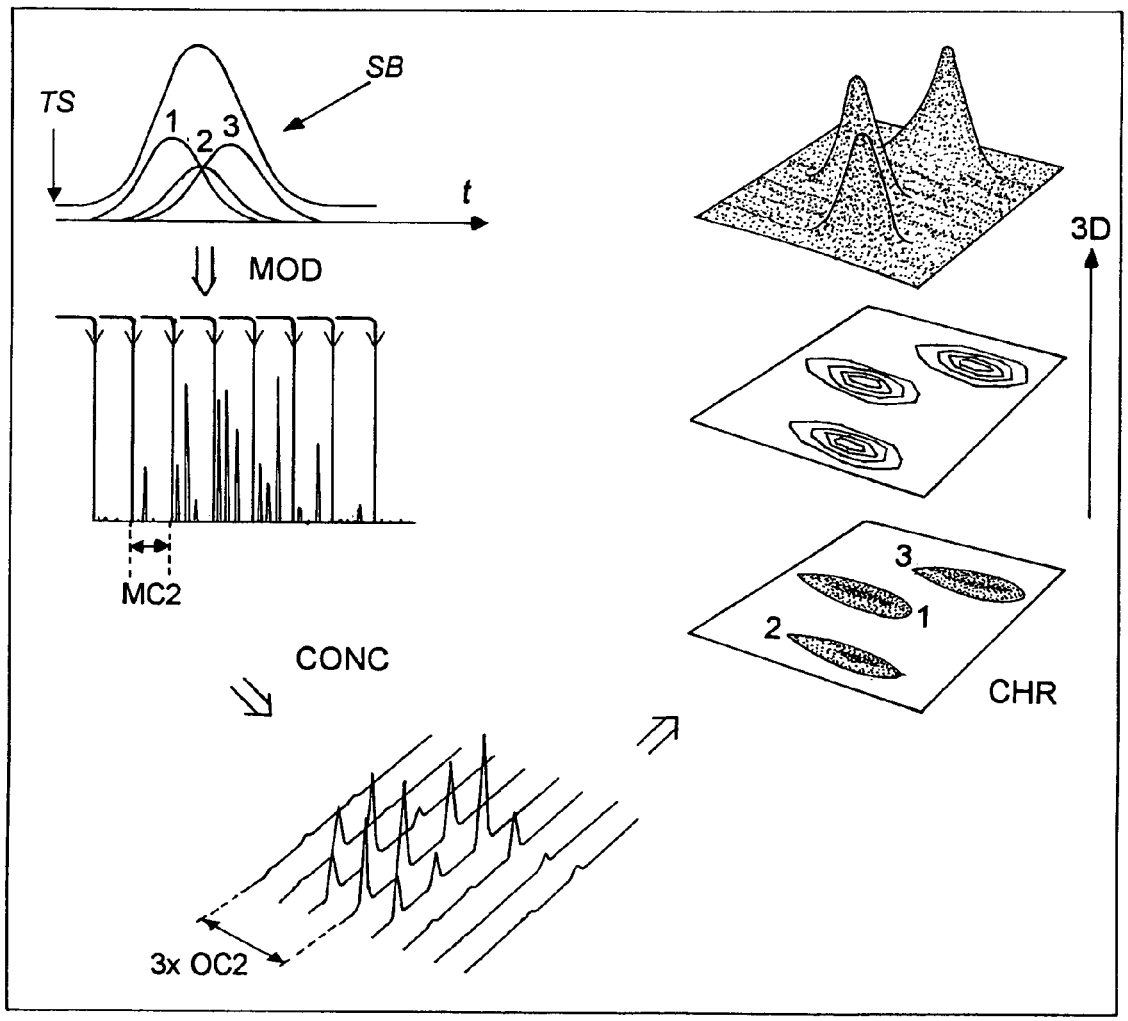
FIG. 1 illustrates the principle of reconstruction of a chromatogram in GC-2D.

The invention relates to a method of determining the physical properties of a petroleum sample. These macroscopic physical properties are observed at the scale of the sample. They can be for example:

Combustion Properties:

octane number (research or motor (RON or MON), property measured on gasolines), cetane number (CN, property measured on diesel fuels),
smoke point (property measured on kerosenes),
gravity (at 15° C.),
Cold Properties:
cold filter plugging point (CFPP),
cloud point,
pour point,
freezing point (property measured on kerosenes).

According to the method, the value of a given physico-chemical property is determined from the molecular composition of the sample, obtained from two-dimensional gas chromatography (GC-2D). The method comprises three major stages:

A—carrying out two-dimensional gas chromatography of the petroleum sample and constructing a two-dimensional chromatogram;

B—determining the concentrations of the compounds contained in the sample, from an analysis of the chromatogram; and C—calculating the physico-chemical properties from these concentrations.

A—Two-Dimensional Gas Chromatography

Two-dimensional gas chromatography (GC-2D) is a particularly efficient separative technique for performing detailed molecular analyses. This technique well known as, for example, described in U.S. Pat. Nos. 5,135,549 and 5,196,039. These documents describe the principle of continuous coupling of two different separation columns in order to obtain two-dimensional chromatograms. An implementation of two-dimensional gas chromatography is for example described in: L. Mondello, A. Lewis, K. Bartle, "Multidimensional Gas Chromatography", Ed. Wiley, 2002.

Two-dimensional gas chromatography is a separative technique wherein all the eluted compounds from a first column are successively subjected to separation in a second column of different selectivity. The two columns are connected in series by means of a modulator which is the key element of the device. This interface samples the effluent of the first column in a form of chemical impulses and transfers them to the second column. The time necessary for this operation, referred to as modulation period, generally requires a very fast second separation (some seconds): the characteristics of the second column are so selected that each impulsion is separated during the modulation period.

The more the compound has affinities with the stationary phase, the more time it will need to leave each column. At the outlet of the second column, the compounds encounter a detector. This device measures various physical properties of a gas mixture in form of a time-dependent intensity. This signal, referred to as chromatogram signal, or raw 1D signal, comprises a set of peaks characteristic of each constituent, whose shape depends on the intensity of the property measured. Each peak is called "elution peak" or "chromatographic peak". The maximum of the intensity corresponding to a peak is referred to as retention time. The signal thus recorded can be of a different nature depending on the detector used. The detectors (TCD, FID, SCD, NCD) are selected according to the type of application by the person skilled in the art. Some detectors allow detection of some ppm (parts per million) of a component.

The elution peak from the first column (1-A) is periodically sampled by the modulator. Each fraction is focused, then continuously injected into the second column. The signal detected, the raw 1D signal, thus corresponds to a succession of separations (materialized by peaks on the signal) carried out in the second dimension (1-B). By placing these chromatograms side by side with an offset, it is possible to reconstruct a signal in two dimensions: the 2D chromatogram.

The image to which the analysis method is applied is a two-dimensional chromatogram. Such a chromatogram is characterized by the following elements:

the modulation period (MC2): time required for sampling the effluent of the first column in a form of chemical impulsions and for transferring them to the second column, the temporal coordinate of the first point taken into account (TS: Time Start). This point is selected by the user (the signal starts are sometimes unexploitable), the second column offset (OC2).

This chromatogram is constructed as follows:

during the two-dimensional gas chromatography, a raw 1D signal corresponding to the signal recorded by the detector at the outlet of the second column as a function of time (t) is recorded. Such a raw 1D signal (SB) consists of a set of points P(t);

the points of this raw 1D signal (SB) having a temporal coordinate smaller than TS+OC2 are removed from the signal;

the signal is divided (MOD) into successive pieces of length MC2; and these pieces are concatenated (CONC) vertically side by side so as to form a 2D image referred to as 2D chromatogram.

This 2D chromatogram is the commonest representation, it thus consists of a set of slices (of width equal to the modulation period MC2) of raw data concatenated side by side. FIG. 1 diagrammatically shows the principle of reconstruction of a chromatogram in GC-2D and a 2D chromatogram (CHR) thus obtained. The two axes of the separation plane indicate the temporal separation coordinates for the first column in abscissa and for the second column in ordinate. Chromatographic peaks then form spots whose intensity is translated into a gradation of colors. This representation is akin to a molecular image of the sample.

Carrying out these operations amounts to applying the following formulas to each point P(t) of the raw 1D signal (SB) having a temporal coordinate greater than TS+OC2:

$$x = MC2 * \text{floor}((t-TS-OC2)/MC2) + TS + OC2 \qquad (1)$$

$$y = \text{mod}((t-TS-OC2); MC2) \qquad (2)$$

with:

t: a temporal position of point P(t) on the raw 1D signal, x and y: the spatial coordinates on the 2D chromatogram of point P(t), floor: a function that returns the greatest integer that is not greater than the argument, mod: function that returns the rest of a division.

It can be noted that the relations expressed above ((1) and (2)), which allow calculation of the spatial coordinates (x,y) of a point P(t) from its temporal coordinates, are reversible: t=x+y. This relation connecting the absolute time (t) and the coordinates (x,y) of a point in the image is kept for any point appearing in this image (2D chromatogram), whether resulting from the raw 1D signal (SB) or from the definition of a polygon.

However, the results from a two-dimensional gas chromatography (GC-2D) have to be coupled with complex data analysis methods.

B-Chromatogram Analysis

The precondition for the calculation of macroscopic properties obtains the concentration of the molecular compounds separated on the two-dimensional chromatogram, in an accurate, repeatable and non-operator dependent manner.

A particularly advantageous technique for interpreting a two-dimensional gas chromatography meeting these conditions is described hereafter. This method mainly comprises three stages:

1—defining the spots of the chromatogram by polygons, referred to as blobs, which correspond to one or more chemical components;
2—adjusting the polygons to the spots identified in the chromatogram;
3—determining the molecular composition of the sample by analyzing the polygons.

1—Definition of the Spots by Polygons in the Chromatogram

The 2D constructed chromatogram exhibits spots whose intensity are translated into a gradation of colors and which represent the chromatographic peaks. The surface area of these spots is proportional to the amount of a specific molecular compound. A spot is an area of the 2D chromatogram comprising at least one elution peak. These spots are referred to as blobs by specialists. It is thus advisable to first define these areas. This definition forms a polygon.

Two options can be considered. Either the polygons are created manually by a person who interprets the 2D image, or a polygon mask, that is a set of predetermined polygons, is applied. Such a mask can result from a prior analysis of a similar solute for example.

In the second case, the mask has to be adjusted to the ongoing study. The previous paragraph showed how the 2D image (2D chromatogram) was made up of juxtapositions of segments of the raw 1D signal (SB) drawn vertically. The relation t=x+y that connects the points of the image to those of the raw 1D signal (SB) is valid only for the points in the center of the columns. It can therefore not be applied directly. A horizontal readjustment is required. It replaces each point mouse captured by the user in the closest column:

$$x' = \text{round}((x - OC2 - TS)/MC2) * MC2 + OC2 + TS$$

with round: function returning the closest integer to the number passed as argument.

With a fixed offset of the second column (OC2), a fixed temporal coordinate of the first point is taken into account (TS) and a fixed modulation period (MC2), a bijection t=x+y can be defined. It associates at each time a set of coordinates in the image. The polygons (blobs) are thus stored in the form as follows:

{tk}: temporal coordinates on the raw 1D signal (SB) of the k vertices of the polygon,
OC2: second column offset upon polygon creation,
TS: value of the temporal coordinate of the first point taken into account upon polygon creation, and
MC2: modulation period upon polygon creation.

Storage of the modulation period allows determination if a polygon is coherent with the acquisition parameters of an analysis (same period). Storage of the offset of the second column and of TS allows having at least one configuration wherein the entire polygon is visible in the image. This storage mode allows readily re-applying a polygon mask to a new analysis, even if the offset used is different. The polygon vertex addition, removal or modification functionalities can then be easily implemented: the spatial positions are automatically converted to temporal positions. This data structure then allows to:

have a bijective relation between the image and the raw 1D signal (SB);
be independent of the offset selected by the user. A polygon mask defined with a certain offset can be applied to a new analysis even if it has a different offset; and be able to use the times corresponding to the integration on a raw 1D signal (SB) so as to recalibrate the points in the 2D image.

2—Adjustment of the Polygons to Spots Identified on the Chromatogram

Thanks to the data structure described above, it is possible to apply a polygon mask to a new analysis (independently of the offset). The goal is then to recalibrate the polygons on a new analysis, that is to calibrate them on elution peak start and end times on the 1D signals corresponding to the intersection between the columns of the image and the polygon. Adjustment of the polygons is divided into three distinct stages:

determination of 1D signals (pieces of the raw 1D signal (SB)) corresponding to the intersection between a polygon and the columns of the image;
determination of the elution peaks on this 1D signal; and
adjustment of a polygon on the previously calculated peak start and end times.

3—Determination of the Molecular Composition of the Sample

The spots of the 2D chromatogram represent a set of chromatographic peaks. The surface area of these spots is proportional to the amount of a specific molecular compound.

If all the temporal coordinates of the intersections of the polygon defining the polygon with the columns of the image are known and have been reprocessed according to the aforementioned principles, the surface areas can be calculated simply.

Processing is carried out for each polygon only if the current modulation period is identical to the one stored in the polygon. The surface area calculations are all carried out with an offset calculated in such a way that the polygon is in the center of the image. This allows obtaining for each analysis result files independent of the second column offset.

C—Calculation of the Physico-Chemical Properties

To describe the method of determining the macroscopic physico-chemical properties of a petroleum sample from the quantitative analysis of this sample by GC-2D, the cetane number (IC) and diesel fuel samples are considered.

A GC-2D quantitative analysis of twenty diesel fuel samples is thus carried out. These analyses provide, for each diesel fuel sample, the concentration of the molecular compounds that make up these samples.

A relation f is defined allowing determination of the cetane number (IC) of a sample as a function of the concentration ($C_i$) of these various molecular compounds i:

$$IC = f(C_i) = \sum_{i=1}^{n} IC_i^{adjust} \cdot C_i$$

with:
n the number of molecular compounds separated by chromatography,
$IC_i^{adjust}$ an adjusted value of the cetane number for a compound i.

The values of $IC_i^{ajust}$ are determined as follows:
these values are initialized from $IC_i^{ini}$, the known value of the cetane number for a compound i, independently of its concentration. For example, the cetane number of N-C16 is 100. These initial values are given by the literature or chemical constraints (for example the cetane number of normal paraffins is higher than the cetane number of iso-paraffins). The table below gives some initial values:

| Component name | $IC_i^{ini}$ |
|---|---|
| C13 ISO PARAFFINS | 0.1558 |
| C14 ISO PARAFFINS | 0.6611 |

-continued

| Component name | $IC_i^{ini}$ |
|---|---|
| C15 ISO PARAFFINS | 0.6992 |
| C16 ISO PARAFFINS | 0.4021 |
| C17 ISO PARAFFINS | 0.3354 |
| C18 ISO PARAFFINS | 0.8134 |
| C19 ISO PARAFFINS | 0.8515 |
| C20 ISO PARAFFINS | 0.8896 | diesel fuel samples are analyzed by GC-2D and their cetane number is measured;

the cetane number is calculated by means of relation f; and the values of $IC_i^{ini}$ are adjusted by a least-squares type method by integrating chemical constraints.

The following table gives the adjusted initial values:

| Component name | $IC_i^{ajust}$ |
|---|---|
| C13 ISO PARAFFINS | 0.3894 |
| C14 ISO PARAFFINS | 0.4132 |
| C15 ISO PARAFFINS | 0.437 |
| C16 ISO PARAFFINS | 0.4608 |
| C17 ISO PARAFFINS | 0.4846 |
| C18 ISO PARAFFINS | 0.5084 |
| C19 ISO PARAFFINS | 0.5322 |
| C20 ISO PARAFFINS | 0.556 |

This type of adjustment is performed on a large number of diesel fuel samples so as to determine the adjusted values $IC_i^{ajust}$ of the hydrocarbon compounds likely to be present in a petroleum sample.

An explicit model consisting of function f and of the adjusted values $IC_i^{ajust}$ is thus obtained.

Of course, it is possible to choose another function f and to perform a new adjustment so as to obtain a new model.

It is important to note that this model is valid for any type of diesel fuel and that it can take into account post-processing on the chromatogram (a petroleum cut for example).

Figure 2:
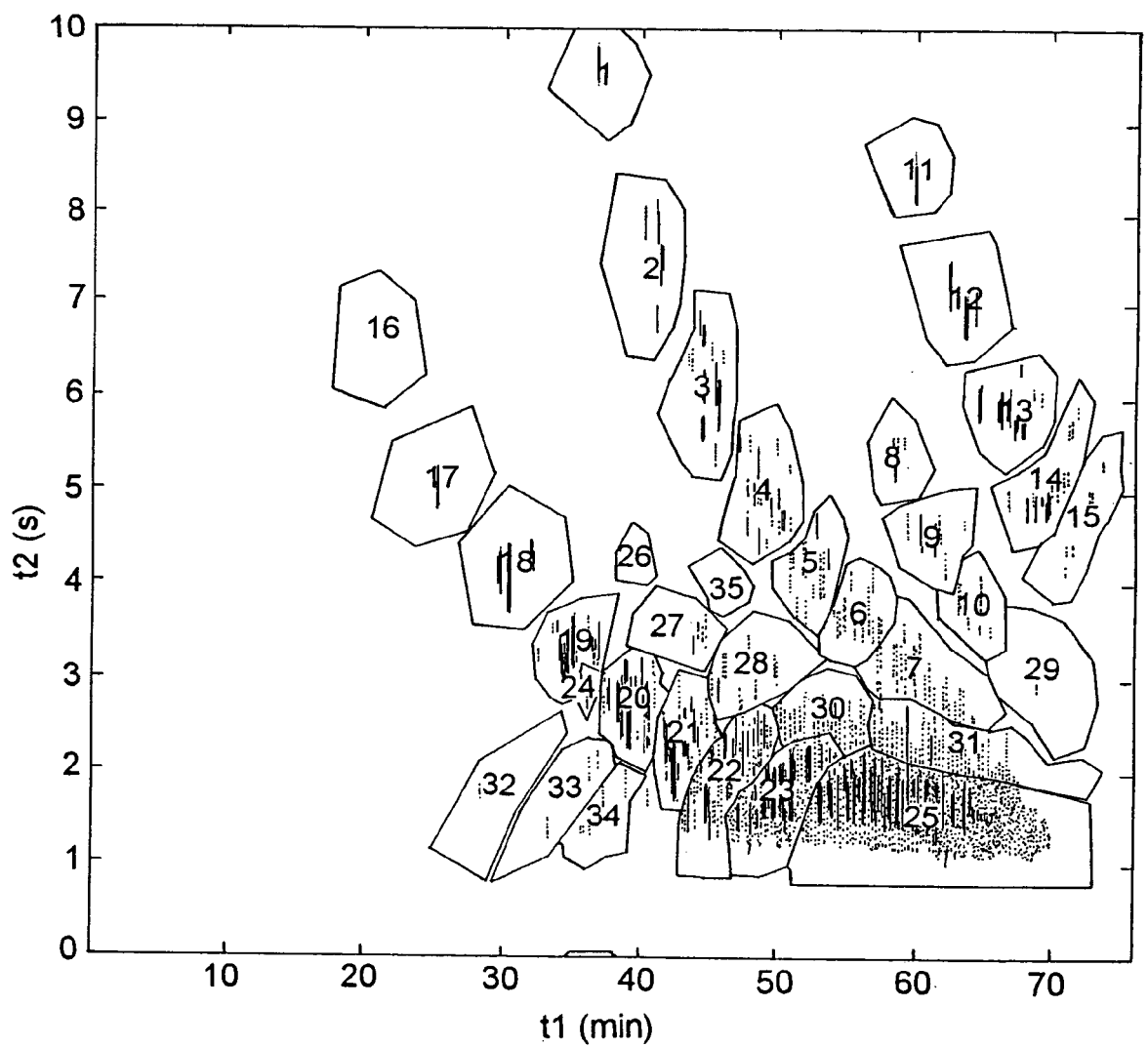
FIG. 2 shows a 2D chromatogram.

Thus, after carrying out a GC-2D analysis on a petroleum sample and constructing a chromatogram such as the one in FIG. 2, blobs (FIG. 2) from which the concentration of each molecular compound is deduced are defined. FIG. 2 shows a 2D chromatogram obtained for the separation of nitrogen-containing compounds contained in a middle distillate sample, the two axes of the separation plane indicating the temporal separation coordinates for the first column in the abscissa and for the second column in the ordinate. Chromatographic peaks then form spots whose intensity is translated into a color gradation. This representation is akin to a molecular image of the sample.

The user then launches the calculations and visualizes:

the final properties of each component after cutting:

| Component name | Family name | Retention time (s) | Boiling point temperature (° C.) | Cetane number |
|---|---|---|---|---|
| C13 ISO PARAFFINS | ISO PARAFFINS | 1923.36 | 217.413005 | 0 |
| C14 ISO PARAFFINS | ISO PARAFFINS | 2663.772 | 250.2371826 | 2.81323018 |
| C15 ISO PARAFFINS | ISO PARAFFINS | 3003.948 | 264.7309332 | 5.769673326 |
| C16 ISO PARAFFINS | ISO PARAFFINS | 3324.09 | 278.7801639 | 4.72741323 |
| C17 ISO PARAFFINS | ISO PARAFFINS | 3684.18 | 294.4823919 | 3.671947351 |
| C18 ISO PARAFFINS | ISO PARAFFINS | 3884.148 | 302.9741152 | 4.285301098 |
| C19 ISO PARAFFINS | ISO PARAFFINS | 4224.282 | 318.0831418 | 4.763893579 |
| C20 ISO PARAFFINS | ISO PARAFFINS | 4644.42 | 336.4711929 | 2.965664768 | the physical properties for each family after cutting:

| Family name | Cetane number |
|---|---|
| DI-NAPHTHENES | 3.159854543 |
| MONO-NAPHTHENES | 19.45162568 |
| MONO-AROMATICS | 11.4218426 |
| DI-AROMATICS | 8.952249288 |
| TRI-AROMATICS | 1.43685633 |
| TETRA-AROMATICS | 0 |
| NAPHTO-MONO-AROMATICS | 0 |
| NAPHTO-DI-AROMATICS | 0 |
| NAPHTO-TRI-AROMATICS | 0 |
| N-PARAFFINS | 19.15360108 |
| ISO-PARAFFINS | 29.43300901 | the physical properties of the sample after cutting:

| Sum of the blob surface areas | 100 |
|---|---|
| Carbon fraction | 1526.958407 |
| Molecular weight | 21444.61929 |
| Gravity (15° C.) | 93.00903854 |
| Vapour pressure (hPa) | 93.00903854 |
| Cetane number | 93.00903854 |
| RON | 93.00903854 |
| MON | 93.00903854 |
| Olefinic carbon | 0 |
| Aromatic carbon | 1196.754823 |
| Paraffin carbon | 7315.742657 |
| Naphthenic carbon | 788.4063742 |
| Carbon | 7949.283561 |
| Hydrogen | 1351.620292 |
| Sulfide | 0 |
| Oxygen | 0 |
| Nitrogen | 0 |

Figure 3:
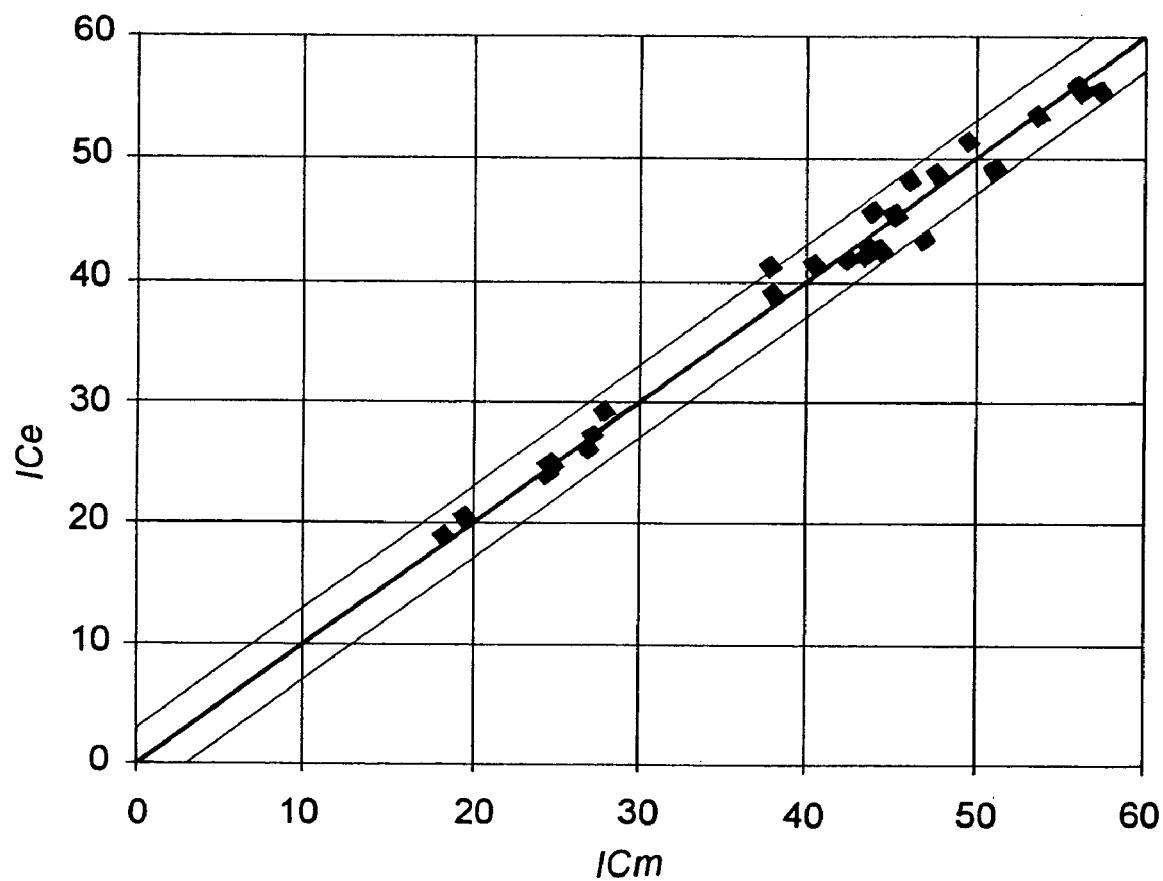
FIG. 3 is an example of prediction of the cetane number of petroleum samples.

FIG. 3 illustrates an example of prediction of the cetane number of petroleum samples. The horizontal axis indicates the cetane number (ICm) measured on a CFR engine and the vertical axis indicates the cetane number (ICe) estimated from the data resulting from GC-2D.

In general terms, according to the invention, the macroscopic physical properties are calculated from the surface area of the various blobs of a 2D chromatogram, these surface areas being representative of the amount of a compound, and they are directly related to the concentrations of the compounds that make up the petroleum sample.

A macroscopic property $P_m$ is calculated from these amounts, by means of a relation f defined by:

$$P_m = f(\alpha_i, Q_i, n)$$

with:
$P_m$: the macroscopic property n: the number of molecular compounds separated by chromatography $\alpha_i$: a previously calibrated coefficient associated with compound i $Q_i$: the amount of compound i determined by chromatography (the concentration for example, or the surface area of the blobs).

Definition of Relation f

Relation f can be defined for example by the relation as follows:

$$f(\alpha_i, Q_i, n) = \sum_{i=1}^{i=n} \alpha_i \cdot Q_i$$

The fact that the macroscopic property of a petroleum sample is a linear combination of the concentrations of each molecular compound of this sample is then expressed.

Calibration of Relation f

This relation is subsequently calibrated. The following stages are therefore carried out:

determining amounts of compounds present in a second mixture (generally a set of petroleum samples is collected) containing at least the n molecular compounds, by means of two-dimensional gas chromatography, measuring the macroscopic property $P_m$ of this second mixture, initializing coefficients $\alpha_i$ by assigning them a known macroscopic physical property value for a sample containing only compound i, calculating the macroscopic physical property by means of function f, modifying coefficients $\alpha_i$ so as to minimize the difference between the value of the calculated macroscopic physical property and the value of the measured macroscopic physical property, and by integrating chemical constraints.

Coefficients $\alpha_i$ of the model can be determined by means of a conventional method of least squares type with constraints so as to minimize the difference between the value of the calculated macroscopic physical property and the value of the macroscopic physical property directly measured on the sample.

According to the embodiment described above, it can be written:

$IC_i^{ajust} = \alpha_i$ and $C_i = Q_i$

Use of Relation f

Once the model is defined and calibrated, that is relation f is defined and the parameters are calibrated, the user has an explicit model defined for chemical compounds. There are therefore no overfitting or overparametrization problems.

This model can thus be used for determining the macroscopic properties of a petroleum sample after analyzing the molecular composition thereof by applying the formula.

Figure 4A:
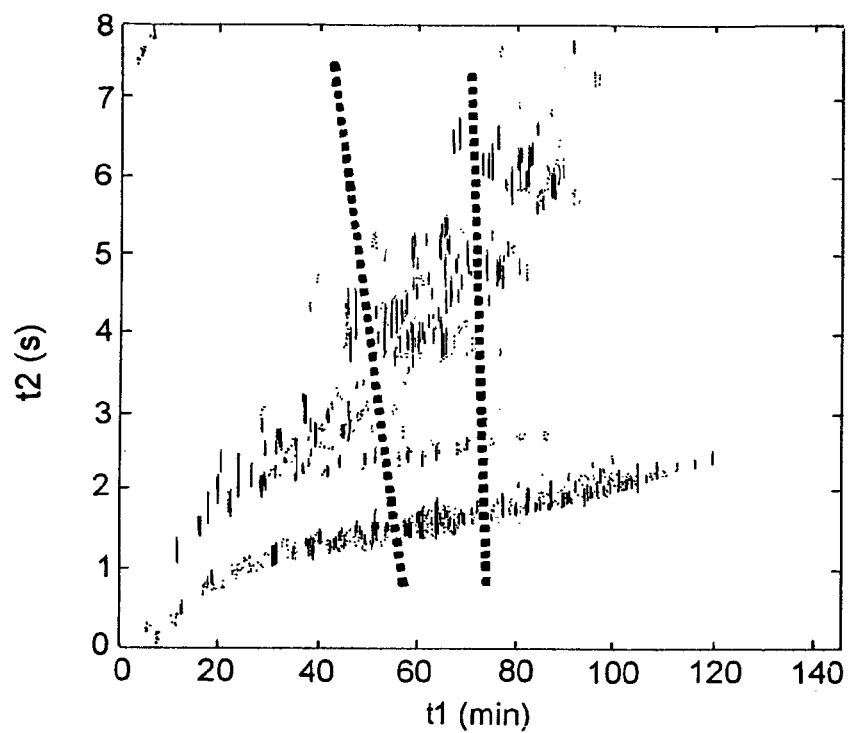
FIG. 4A illustrates the chromatogram of the total sample, the dotted lines represent the 280-310° C. virtual petroleum cut
Figure 4B:
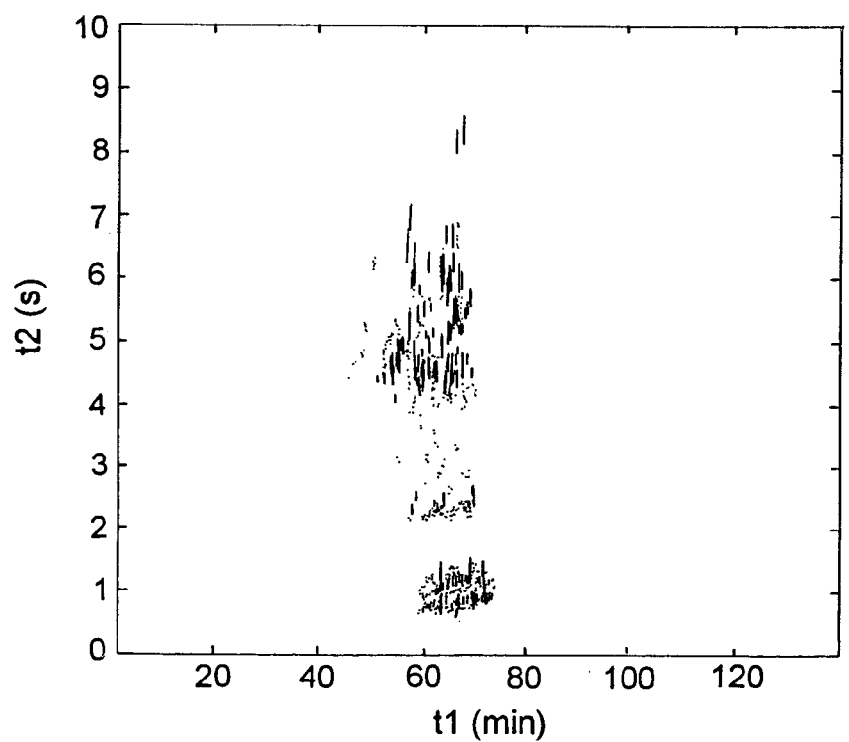
FIG. 4B illustrates the chromatogram of the 280-310° C. real cut obtained by physical distillation of the total sample.

It is also possible to assess the macroscopic properties for any petroleum cut by removing some parts of the chromatogram (cut). The time of the first dimension of the chromatogram is converted to temperature via knowledge of the boiling point temperatures of reference compounds (generally n-paraffins), then only the part of the chromatographic signal corresponding to the cut interval is kept. The macroscopic property is then calculated by means of relation f. FIG. 4 illustrates a chromatogram of a diesel fuel, total effluent of a refining plant. FIG. 4A illustrates the chromatogram of the total sample. The dotted lines represent the 280-310° C. virtual petroleum cut. FIG. 4B illustrates the chromatogram of the 280-310° C. real cut obtained by physical distillation of the total sample. The effect of a change in the distillation range of a sample on the macroscopic property is thus simulated.

The evolution of these properties as a result of chemical transformations of the petroleum sample can also be assessed by simulating the effect of a chemical transformation of a family of compounds on the macroscopic properties.

Advantages

The present invention allows directly carrying out property calculations from the chemical composition of a sample analyzed by GC-2D. Two-dimensional chromatography allows connecting, by means of a one-to-one relation, the property of a blob to its concentration. The predicted macroscopic physical properties are thus independent of any calibration base. They are therefore extrapolatable, and they thus allow prediction of the macroscopic properties of a sample, to assess these properties for any petroleum cut (distillation), and to assess the evolution of these properties after chemical transformations of the petroleum sample (hydrogenation). The method is particularly well suited for petroleum samples distillable between 150° C. and 450° C.

The method is sufficiently generic: any type of property can be calculated. The calculation formula can be linear or not.

The invention claimed is:

1. A method of determining at least one physical property of a mixture of molecular compounds, comprising:

using a two-dimensional chromatography apparatus to determine amounts of compounds present in the mixture; and determining the at least one physical property from the amounts using a previously calibrated relation connecting the at least one physical property to the amounts, and wherein the two-dimensional gas chromatography apparatus includes columns and the method further comprises recording a chromatographic signal comprising chromatographic peaks, generating a two-dimensional chromatogram with each column thereof corresponding to a portion of the chromatographic signal with the chromatographic peaks forming spots on the chromatogram, defining the spots with polygons, adjusting each polygon by identifying portions of the chromatographic signal contained between two intersections of each polygon using columns of the chromatographic peaks present in the portions by displacing the intersections according to the start times, the end times and the chromatographic peak maxima and determining the amount of at least one molecular compound by calculating a surface area of the adjusted polygon.

2. A method as claimed in claim 1, wherein the previously calibrated relation is defined by:

$P_m = f(\alpha_i, Q_i, n)$, wherein f is the previously calibrated relation, $P_m$ is the physical property, n is the number of molecular compounds separated by the two-dimensional chromatography apparatus, $\alpha_i$ is a coefficient to be calibrated and associated with a compound i, and $Q_i$ is the amount of compound i determined by the two-dimensional gas chromatography apparatus, and the relation f is calibrated by the steps:

using the two-dimensional gas chromatography apparatus to determine amounts of compounds present in at least a second mixture containing at least the n molecular compounds;

measuring the physical property $P_m$ of the second mixture;

initializing coefficients $\alpha_i$ by assigning the coefficients a known physical property value for a sample containing only compound i;

calculating the physical property with the function f; and modifying the coefficients $\alpha_i$ to minimize a difference between a value of the calculated physical property and a value of the measured physical property.

3. A method as claimed in claim 2, wherein the relation f is defined by:

$$f(\alpha_i, Q_i, n) = \sum_{i=1}^{i=n} \alpha_i \cdot Q_i.$$

4. A method as claimed in claim 3, wherein an amounts of compounds is determined by assessing a concentration thereof from a surface area of each polygon.

5. A method as claimed in claim 3 wherein:
the mixture of molecular compounds comprises a petroleum sample.

6. A method as claimed in claim 5, wherein an amounts of compounds is determined by assessing a concentration thereof from a surface area of each polygon.

7. A method as claimed in claim 2 wherein:
the mixture of molecular compounds comprises a petroleum sample.

8. A method as claimed in claim 7, wherein an amounts of compounds is determined by assessing a concentration thereof from a surface area of each polygon.

9. A method as claimed in claim 2, wherein an amounts of compounds is determined by assessing a concentration thereof from a surface area of each polygon.

10. A method as claimed in claim 1, wherein the amounts of compounds is determined by assessing a concentration thereof from a surface area of each polygon.

11. A method as claimed in claim 1, wherein the at least one physical property is selected from properties as follows:
at least one of combustion properties comprising octane number, cetane number, smoke point and gravity, or
cold properties comprising cold filter-plugging point, cloud point, pour point and freezing point.

12. A method as claimed in claim 1, wherein the mixture is a petroleum sample distillable between 150° C. and 450° C.

13. A method as claimed in claim 1 comprising:
predicting at least one physical property of a cut of a petroleum sample, wherein an effect of a change in a distillation range of the sample on the at least one physical property is simulated by keeping only a part of the chromatographic signal corresponding to a distillation interval and by calculating the at least one physical property.

* * * * *